(12) United States Patent
Draenert (10) Patent No.: US 9,131,990 B2
(45) Date of Patent: Sep. 15, 2015

(54) ARRANGEMENT AND IMPLANT FOR REPLACING SURFACES THAT ARE SUBJECT TO STRESSES

(75) Inventor: Klaus Draenert, Munich (DE)

(73) Assignee: Karl Storz GmbH & Co. K, Tuttlingen (DE)

( * ) Notice: Subject to any disclaimer, the term of this patent is extended or adjusted under 35 U.S.C. 154(b) by 769 days.

(21) Appl. No.: 10/545,442

(22) PCT Filed: Jun. 5, 2003

(86) PCT No.: PCT/DE03/01880
§ 371 (c)(1),
(2), (4) Date: Aug. 15, 2005

(87) PCT Pub. No.: WO03/103535
PCT Pub. Date: Dec. 18, 2003

(65) Prior Publication Data
US 2006/0015189 A1    Jan. 19, 2006

(30) Foreign Application Priority Data

Jun. 6, 2002   (DE) .................................. 102 25 217

(51) Int. Cl.
*A61B 17/00* (2006.01)
*A61C 1/08* (2006.01)
(Continued)

(52) U.S. Cl.
CPC .............. *A61C 1/084* (2013.01); *A61B 17/1635* (2013.01); *A61B 17/1637* (2013.01);
(Continued)

(58) Field of Classification Search
CPC .............. B23B 51/082; B23B 2251/14; B23B 2251/18; B23B 2251/04; B23B 51/00; B23B 2251/02

USPC ...... 606/86, 96, 86 A, 86 R, 80–83, 167, 168, 606/171, 177–180; 623/23.44, 17.17
See application file for complete search history.

(56) References Cited

U.S. PATENT DOCUMENTS 3,879,767 A  *  4/1975  Stubstad .................... 623/21.19
4,312,079 A      1/1982  Dorre et al.
(Continued)

FOREIGN PATENT DOCUMENTS

DE       2411618       4/1975
DE       2953575       7/1982
(Continued)

OTHER PUBLICATIONS

"Elliptical". The Online Plain Text English Dictionary [online], [retreived on Apr. 11, 2007]. Retrieved from the Internet: <URL: www.onelook.com>.*
(Continued)

*Primary Examiner* — Mary Hoffman
*Assistant Examiner* — Tara R Carter
(74) *Attorney, Agent, or Firm* — Westman, Champlin & Koehler, P.A.

(57) ABSTRACT

An implant for partially replacing surfaces that are subject to stresses includes a base that is inserted into an area removed from a bone. The base includes at least one surface for replacing the removed area of the bone and an adapter for receiving the base. The system for inserting the implant includes an angle determining system that includes a set of elliptical plates having different diameters to determine the cutting angle of the implant to be utilized to replace the surface of the bone. The system also includes an oscillating drill with hollow drills that have beveled tips.

13 Claims, 8 Drawing Sheets

(51) Int. Cl.
*A61B 17/16* (2006.01)
*A61B 17/17* (2006.01)
*A61C 8/00* (2006.01)
*A61F 2/30* (2006.01)
*A61F 2/38* (2006.01)
*A61F 2/28* (2006.01)

(52) U.S. Cl.
CPC ............ *A61B17/1714* (2013.01); *A61C 8/001* (2013.01); *A61C 8/0089* (2013.01); *A61F 2/30756* (2013.01); *A61B 17/1675* (2013.01); *A61B 17/1764* (2013.01); *A61F 2/3859* (2013.01); *A61F 2002/2839* (2013.01); *A61F 2002/3023* (2013.01); *A61F 2002/30242* (2013.01); *A61F 2002/30329* (2013.01); *A61F 2002/30433* (2013.01); *A61F 2002/30492* (2013.01); *A61F 2220/0025* (2013.01); *A61F 2220/0041* (2013.01); *A61F 2230/0067* (2013.01); *A61F 2230/0069* (2013.01); *A61F 2230/0071* (2013.01); *A61F 2310/00023* (2013.01); *A61F 2310/00179* (2013.01); *A61F 2310/00293* (2013.01)

(56) References Cited

U.S. PATENT DOCUMENTS

| | | | |
|---|---|---|---|
| 4,479,271 A | | 10/1984 | Bolesky et al. |
| 4,531,917 A | * | 7/1985 | Linkow et al. ............... 433/176 |
| 4,696,298 A | * | 9/1987 | Higgins et al. ............... 606/171 |
| 4,784,124 A | * | 11/1988 | Kaltenbrunner et al. ....... 606/63 |
| 4,784,661 A | * | 11/1988 | Beckenbaugh et al. ... 623/21.12 |
| 4,811,632 A | * | 3/1989 | Salyer ............................ 76/115 |
| 4,911,720 A | * | 3/1990 | Collier ...................... 623/23.12 |
| 5,194,066 A | * | 3/1993 | Van Zile ................... 623/20.15 |
| 5,320,115 A | * | 6/1994 | Kenna .......................... 128/898 |
| 5,326,364 A | * | 7/1994 | Clift et al. ................. 623/21.11 |
| 5,330,533 A | | 7/1994 | Walker |
| 5,368,051 A | | 11/1994 | Dunn et al. |
| 5,423,330 A | * | 6/1995 | Lee ................................ 600/566 |
| 5,570,700 A | * | 11/1996 | Vogeler ......................... 600/567 |
| 5,591,170 A | * | 1/1997 | Spievack et al. ............... 606/82 |
| 5,702,471 A | | 12/1997 | Grundei et al. |
| 5,772,664 A | | 6/1998 | DeSatnick et al. |
| 5,881,733 A | | 3/1999 | Stone |
| 5,921,987 A | | 7/1999 | Stone |
| 6,013,853 A | | 1/2000 | Athanasiou et al. |
| 6,039,568 A | * | 3/2000 | Hinds .......................... 433/175 |
| 6,200,322 B1 | * | 3/2001 | Branch et al. ................... 606/96 |
| 6,284,002 B1 | * | 9/2001 | Sotereanos ..................... 623/27 |
| 6,315,795 B1 | | 11/2001 | Scarborough et al. |
| 6,344,043 B1 | | 2/2002 | Pappas |
| 6,375,658 B1 | | 4/2002 | Hangody et al. |
| 6,530,928 B1 | | 3/2003 | Frei et al. |
| 2003/0135219 A1 | * | 7/2003 | Salyer et al. .................... 606/81 |
| 2003/0170591 A1 | | 9/2003 | Kurer |
| 2005/0038442 A1 | * | 2/2005 | Freeman ......................... 606/86 |

FOREIGN PATENT DOCUMENTS

| | | |
|---|---|---|
| DE | 2953575 A1 | 7/1982 |
| DE | 197 21 661 | 11/1998 |
| DE | 19839950 | 1/2000 |
| DE | 200 19 026 | 3/2002 |
| EP | 1159923 | 5/2000 |
| FR | 2700462 | 7/1994 |
| JP | 2920167 | 7/1999 |
| JP | 11347039 | 12/1999 |
| WO | WO 95/19141 | 7/1995 |
| WO | 9627333 | 9/1996 |
| WO | WO 98/52498 | 11/1998 |
| WO | WO 99/21497 | 5/1999 |
| WO | 0132109 A1 | 5/2001 |
| WO | 01/80772 A1 | 11/2001 |
| WO | 0180772 A1 | 11/2001 |

OTHER PUBLICATIONS

"Bevelled". The Online Plain Text English Dictionary [online], [retreived on Apr. 11, 2007]. Retrieved from the Internet: <URL: www.onelook.com>.*

International Search Report—PCT/DE 03/01880. (German and English copies).

Communication dated Dec. 14, 2010, from the European Patent Office in corresponding European Patent Application No. EP 03 756 969.6.

Communication dated Mar. 2, 2012, from the European Patent Office in corresponding European Patent Application No. EP 03 756 969.6.

Communication dated Sep. 28, 2012, from the European Patent Office in corresponding European Patent Application No. EP 03 756 969.6.

Communication dated Mar. 18, 2013, from the European Patent Office in corresponding European Patent Application No. EP 12 19 9267.1.

Communication dated Mar. 20, 2013, from the European Patent Office in corresponding European Patent Application No. EP 12 19 9263.0.

Search Report issued by the European Patent Office dated Mar. 5, 2014, in corresponding European Patent Application No. EP 12 19 9263.0 (10 pages).

* cited by examiner

ARRANGEMENT AND IMPLANT FOR REPLACING SURFACES THAT ARE SUBJECT TO STRESSES

CROSS-REFERENCE TO RELATED APPLICATION

This. Application is a Section 371 National Stage Application of International Application No. PCT/DE03/01880, filed Jun. 5, 2003 and published as WO 03/103535 on 18 Dec. 2003, in German.

FIELD OF INVENTION

The present invention relates to an arrangement especially for the partial replacement of surfaces that are subject to stresses, e.g. the surfaces of a joint. However, it can also be used to replace jaw areas supporting chewing surfaces including teeth or pins.

BACKGROUND OF THE INVENTION

Until now, when joint surfaces became worn, it was usual to replace the entire joint or joint parts in toto with an endoprosthesis.

SUMMARY OF THE INVENTION

The object of the present invention is to create implants and an arrangement that allow partial replacement of surfaces that are subject to stresses, such as chewing or joint surfaces, without requiring the insertion of an entire endoprosthesis.

The novel implants and arrangements follow the principle that first the size of the defective joint surface section is determined, a drilling area is calculated within which the bone is removed with a special drilling device, the removed area of the bone also including the defective joint surface, and the removed bone area is subsequently replaced with an implant, e.g. with an inorganic base such as hydroxy apatite or with composite materials such as tricalcium phosphate with grafted bone or cartilage tissue or with a joint surface material or bone replacement material known in the prosthetics industry, such as ceramic or metals, particularly titanium alloys.

The implant according to the invention includes a spherical or axial base. An axial base is any base that has a longitudinal or symmetrical axis: Such bases are particularly cylinders with different footprints (circle, ellipse, polygon), cones, subrings or similar elongated bases. Spherical bodies do not have to have an exactly spherical shape. Its extension may be slightly different in all three spatial directions, e.g. ellipsoid, egg- or breadroll-shaped, etc. The base includes at least one surface that is formed as a joint replacement surface and/or has an adapter for accepting a surface element with such a surface.

In the rest of this document, joint surfaces will be used to designate other stressed surfaces as well, such as the chewing surfaces of a tooth. The base is inserted in an area of removed bone, from which the bone has been removed previously e.g. by drilling, punching, milling, via a laser and by other comparable removal techniques. The base is preferably held in place in the removed area by an interference fit, although other means of fixing with friction fit or positive locking, e.g. screwed, are also conceivable. The base may for example be cylindrical in shape and may support the joint surfaces directly or it may have an adapter for receiving such an element, such as a hole for receiving a tooth or pivot tooth or the frontal or peripheral part of the joint surface.

The implants according to the invention preferably include a cylindrical base with two frontal faces facing away from one another, of which the first frontal face or the periphery of the base preferably has a straight or curved surface at an angle not equal to 90 degrees to the axis of the cylinder, forming the joint surface to be replaced, and the second frontal face also has a preferably straight or curved surface at an angle not equal to 90 degrees to the axis of the cylinder, which closes with the bone periphery after it has been implanted. Instead of the surface, the base may also have an adapter for receiving one of the surface elements that contains the surface to be replaced, e.g. a joint surface element or tooth. However, the angle of the surface(s) may also be 90°.

The joint surfaces are preferably surface treated so that the natural joint surface structure is reflected as accurately as possible. Parts of the implant that come into contact with the bone or surrounding tissue may be coated and/or faced with antibiotics in a method known per se to prevent inflammations. In the same way, bone replacement materials may be manufactured from a correspondingly treated material, e.g. formed or sintered.

The implant preferably fits in the punched out or drilled out bone area in such a way that it is held by the interference fit. The cylindrical diameter of the implant is then preferably minimal, e.g. 0.01 to 0.5 mm larger than the drill hole in the bone. The fact that the forces acting on the joint surface are not transferred to the implant axially, but at a certain angle is advantageous for the interference fit. Of course, the cylindrical barrel of the implant may also be roughened or be provided with a clasping structure, e.g. a thread, which however is disadvantageous with regard to traumatizing the surrounding bone tissue.

The implant is preferably a single part, in other words it is produced from one material in one manufacturing step, which simplifies production. However, it may also be provided that the cylindrical base and the second frontal face are made from a conventional bone replacement material, while the first frontal face, which forms the joint surface is formed by a special joint surface material, such as special titanium alloys or ceramic. Alternatively, both frontal faces may also be made from a different material than the cylindrical implant base.

If the base has an adapter for the surface element, the function of the base as a bone replacement substance may be optimized, while the received surface element may be optimized as a joint surface element. The selection of the material must be modified accordingly. All known screwed attachment methods or other positive locking techniques, friction or interference fit are suitable as adapter combinations.

The shape of the implant or joint surfaces, e.g. on at least one of the two frontal faces may be reproduced to match the drilled out or punched out bone part in a shape tracing method known per se, wherein it must be ensured that the diameter of the base is enlarged such that the implant base is held securely in an interference fit in the bone.

All commonly used implant materials and bone replacement materials are suitable for producing the implant.

An arrangement for inserting the implant according to the invention preferably includes an angle determination system in the form of elliptical plates. The shape of the elliptical plates corresponds to the intersecting plane through a circular cylinder at a given angle of intersection x relative to the plane perpendicular to the axis of the cylinder. The greater the angle of intersection, the longer the ellipse. The width of the ellipse is conserved through the diameter of the circular cylinder. Elliptical plates are provided, preferably with different diameters and different angles of intersection. The reason these elliptical plates have different geometries is so that a suitable elliptical plate may be selected to cover a defect in such a way that while it covers the defective joint surface area completely, at the same time it covers as little of the healthy joint surface as possible. When the correct elliptical plate has been found, the angle of intersection of the elliptical plate indicates the exact drilling angle and drilling diameter for the bone material to be removed and replaced, drilling in the corresponding angle and the corresponding diameter being set in such a way that drilling ends in the defective joint surface area.

To enable corresponding substitution of the bone material, the arrangement according to the invention further includes an angle guiding device that has a fixing extension for insertion between the joint surfaces. This fixing extension may be for example the angle determining arrangement or any other extension that enables the angle guiding device to be fixed between the joint surfaces. An angle adjusting device is linked to the fixing extension and includes a guide element or bore guide that either extends relative to the fixing extension at the angle defined by the elliptical plate or whose angle is adjustable to the angle of intersection defined by the elliptical plate.

The guide element on the angle adjusting device is arranged at the adjusted angle relative to the fixing extension and enables setting of a guide wire in the 30 operational area for fastening a bore guide, which enables a drill to be guided through the bone at the preset angle so that it ends exactly in the joint surface to be replaced. After setting the guide wire, the bore guide is fastened by the guide wire at the prescribed angle and distance from the defective joint surface, and then the tubular drill for removing the bone material is guided into the bone area to be cut away by this bore guide.

Instead of the guide element for setting the guide wire, the bore guide may also be provided on the angle adjusting device, in which case the tubular drill for removing the bone material is guided into the bone via the angle adjusting device itself.

A drilling arrangement for removing the bone material or for drilling the path includes a drill and/or a punch, which may be guided by a bore guide. The bore guide is held either by the guide wires or the angle adjusting device itself at a fixed angle relative to the joint surface section to be restored in such a way that the drilling axis ends in the center of the joint surface section to be replaced.

To create a clean cut that ends exactly in the plane of the joint surface, the drilling arrangement preferably includes an oscillation drill device that has a hollow tubular drill with a beveled tip, the bevel of the tip corresponding exactly to the drilling angle of the drill relative to the joint surface. The oscillation angle of the oscillation drill device is exceptionally small, preferably less than 10°, especially less than 5°. In this manner, it is possible to guide the drill via the drilling device or drilling machine directly to the joint surface, wherein the beveled tip lies exactly parallel to the joint surface, so that one edge of the drill is not already cutting into the facing joint surface when the opposite drill edge has just reached the joint surface.

The tubular drills themselves are preferably designed as thin-walled, hollow cylindrical drills whose beveled tips have a hard runner back, which is especially coated with grindstone or carbide trimming, especially with a diamond trimming, so that the sharpness of the drill is guaranteed even after frequent use and the bone tissue is traumatized as little as possible.

DETAILED DESCRIPTION OF THE PREFERRED EMBODIMENTS

Figure 1:
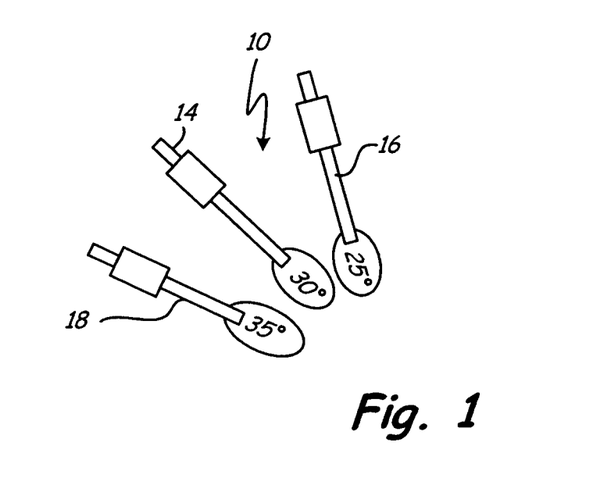
FIG. 1 shows a set of elliptical plates for determining the drilling size and the drilling angle.
Figure 2:
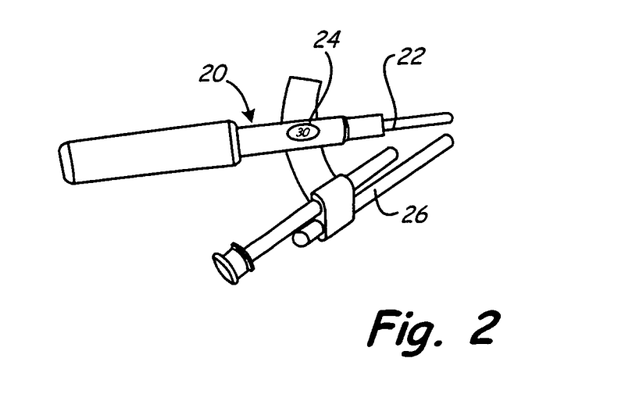
FIG. 2 shows an angle guiding device whose fixing extension is formed by an elliptical plate.

FIG. 1 shows three elliptical plates which are obtained from a circular cylinder by a diagonal cut. The angle determination from the elliptical plates then specifies the angle of intersection relative to a cross-sectional area to the cylinder axis. Accordingly, a large angle deviation from the cylinder cross section requires a correspondingly longer elliptical shape and a smaller deviation requires a correspondingly shorter ellipse. The width of the ellipse corresponds to the cylinder diameter.

The set of elliptical plates to be provided includes different angles as well as different diameters, so that all sizes of joint surface defects may be covered with the elliptical plates. The elliptical plates are arranged over the defective joint site in such a way that the entire defective joint surface but at the same time as little of the healthy joint surface as possible is covered. The angle and width, in other words the diameter of the elliptical plate, determine the drilling angle and the diameter of the drill that will be used to remove the bone material. The removal of the bone occurs at the angle specified by the elliptical plate relative to the joint surface, the drilled or punched cylinder area ending in the defective joint surface, This drilled or cut out or punched out bone area is replaced afterwards with naturally-based bone replacement material such as hydroxy apatite, or by ceramic or metallic implant materials e.g. with a titanium base, wherein the end of the bone replacement material projecting into the joint surface then replaces the defective joint surface that was cut out.

Instead of the elliptical plates, it is also possible to determine the correct angle of intersection and drilling diameter for the bone material to be removed by measuring the length and the width of the defective site.

Additionally, the system according to the invention for partial joint surface restoration includes an angle guiding device which either enables the drill to be guided through the bone at the desired angle relative to the joint surface, or the guide wires to be set to which a bore guide may be attached, the bore guide then having the task of guiding the drill in the appropriate manner. The drill hole is set in such a way that it passes through the bone in the previously determined distance and angle and ends at the defective site, so that the defective site in the joint surface is removed from the bone by the drilling process.

Figure 3:
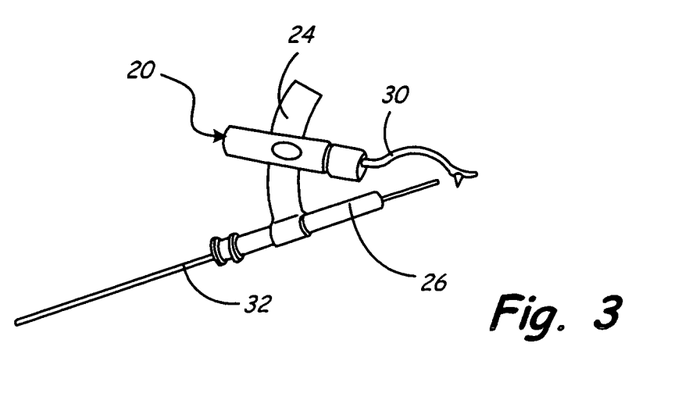
FIG. 3 shows an angle guiding device in which the fixing extension is configured for knee joints by a fixing mandrel.
Figure 4:
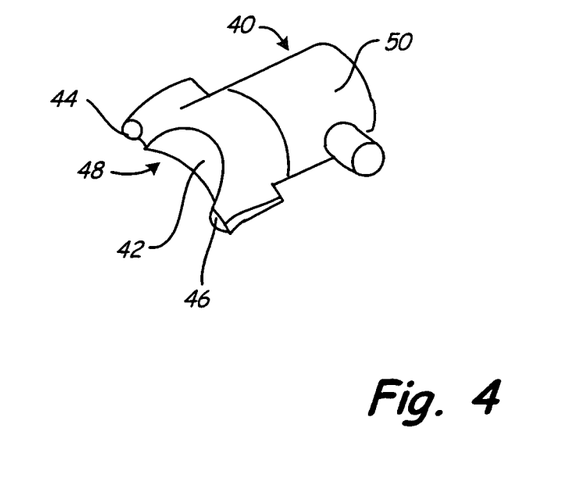
FIG. 4 shows a bore guide.

For this purpose, angle adjusting device 20 has a fixing extension 22, which in this case is formed by an elliptical plate from FIG. 1, an angle adjusting mechanism 24 and a guide 26 for setting guide wires in the bone. In addition, angle adjusting device 20 has a handle 28 at its back end for better handling. Fixing extension 22 is preferably secured detachably in angle adjusting device 20 so that different fixing extensions may be used in angle adjustment device 20, as is shown in exemplary manner in FIG. 3, in which fixing extension 30 is configured for used in the knee joint by a fixing mandrel. FIG. 3 also shows a guide wire 32, which is set in the bone by guide element 26 to fix a bore guide to the bone, the bore guide being shown in FIG. 4, for example.

Bore guide 40 includes a contact area 42 for attaching to the bone and two guide holes 44, 46 through which guide wires 32 may pass. The guide wires are set in the bone e.g. via the angle adjusting device 20 of FIGS. 2 and 3. Bore guide 40 is formed entirely as a hollow cylinder with an inner cylinder area 48, in which a drill is guided as shown FIGS. 5 to 8. Bore guide 40 also includes a swiveling sleeve 50 that has clamping elements (not shown) for fixing a guided drill into a defined position.

Figure 5:
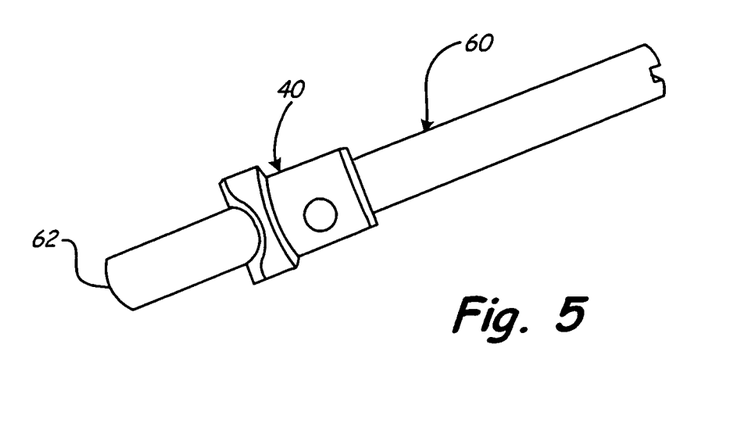
FIG. 5 shows a bore guide with a tubular drill.

FIG. 5 shows a bore guide 40 together with a tubular drill 60, which has a diamond tip 62. Tubular drill 60 has very thin walls and a hollow interior, to that the bone material is only cut in the footprint area of tubular drill 60, while the material to be removed remains inside the inner cavity of the drill. Trauma to the tissue is thus kept to a minimum.

Figure 6:
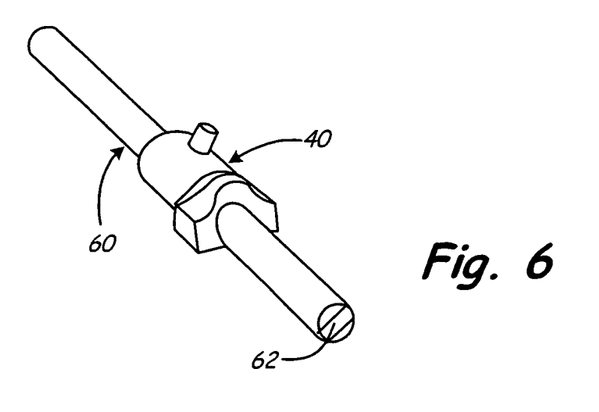
FIG. 6 shows a second perspective view of the bore guide with the tubular drill of FIG. 5.

FIG. 6 shows a diagonal front view of the same arrangement with bore guide 40 and tubular drill 60.

If the bone is to be drilled at an offset angle, an oscillation drilling device with a small oscillation angle of no more than 10°, especially no more than 5° is preferably used. In this case, the tip of tubular drill 64, 66 is preferably beveled 68, 70 so that the elliptical surface of the drill head that is formed by the bevel ends exactly on the plane of the joint, which ensures that when the bone material is removed, i.e. punched out, the edge of the drill does not cut into the tissue between the joint surfaces or into the intact joint surface opposite. With the small oscillation angle in conjunction with the bevel of the tubular drill adjusted to the angle of intersection, it is thus ensured that the front end 68, 70 of the drill ends exactly at the plane of the joint. If the punched out material is still hanging on by a few fibers, a set 80 of hand drills 82 to 86 (FIG. 8) is preferably provided, whose beveled tips 88 to 92 exactly match the inclined surface of drills 64, 66 of FIG. 7 and have the exact elliptical shape of the elliptical plates of FIG. 1. With manual drills 82 to 86, the punched bone material may thus be gently released from the operation field.

Figure 9:
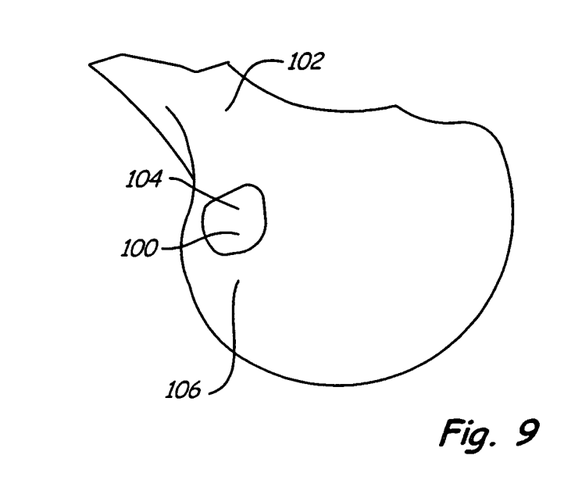
FIG. 9 shows a schematic view of the advance of the tubular drill with beveled tip in the operation zone, FIG. 10/11 shows a schematic representation of the punching and replacing of a defective joint surface area.

After drilling out and removing the bone material, an implant 100 is then inserted into the bone 102, as shown in FIG. 9, wherein the material of the implant is surface treated on the joint side frontal face 104 and on the outer side of the bone 106 thereof, in order to reproduce the shape and smoothness of the joint surface as naturally as possible, and also to match the outer surface of the bone as closely as possible to prevent trauma to the surrounding tissue.

Figure 10:
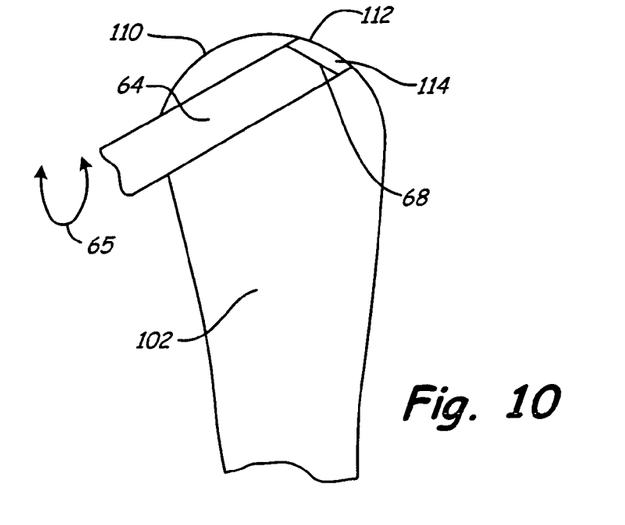
Figure 11:
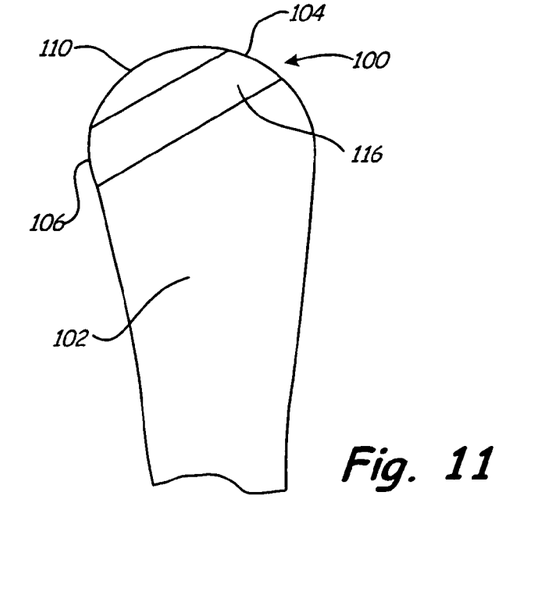

The operation of boring with the oscillation drill device and the subsequent replacement of the punched bone area with an implant is shown schematically in FIGS. 10 and 11.

Figure 7:
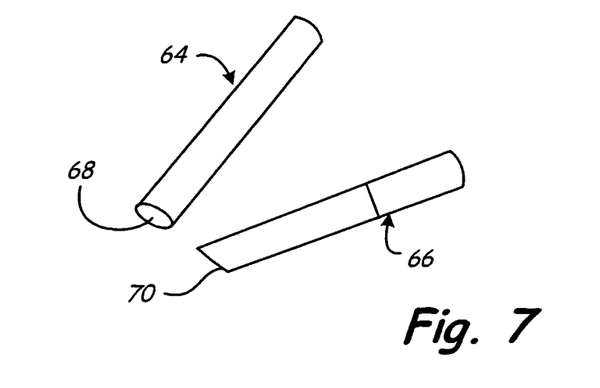
FIG. 7 shows the side view of a two cylinder drill with beveled tip.
Figure 8:
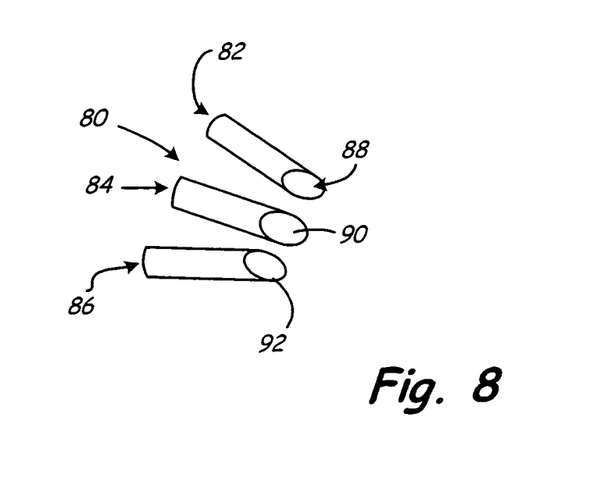
FIG. 8 shows a tubular drill with a beveled tip for manual operation.

FIG. 10 shows a bone 102 with an upper joint surface 110, e.g. corresponding to the ball-and-socket joint of the femur. With a hollow tubular drill 64 as shown in FIG. 7 having a beveled tip 68, the bone material to be removed is now punched out below the defective joint surface area 112. If an oscillation drill device 65 with a small oscillation angle of approximately 5 degrees is used, bevel 68 remains approximately parallel to the surface of defective joint surface section 112. Now when the beveled tip 68 of hollow cylinder punch 64 reaches surface 112, it lies almost exactly on the plane of defective section 112 and only minimally traumatizes the tissue surrounding the joint.

As shown in FIG. 11, after the removal of the bone material 114 to be replaced, the resulting cylindrical drill hole in bone 102 is filled by an implant 100, such has was shown in FIG. 9 for example.

The implant includes a cylindrical base 116, whose surfaces facing away 104 and 106 replace defective joint surface area 112 and the bone periphery. Frontal face 104 of implant 100 facing the joint is surface treated to reproduce the geometry and surface constitution of the surrounding joint surface area 110 as exactly as possible. Shape reproduction procedures that are known per se may also be used for reproducing the frontal face 104 of the surface joint from surface joint area 112 as accurately as possible. Frontal face 106 of implant 100 facing the bone periphery is also surface treated to create a homogeneous and tissue-tolerant closure with the surrounding bone surface.

Figure 12:
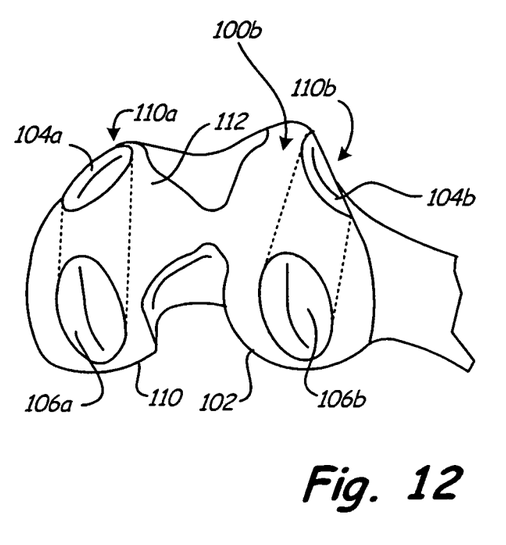
FIG. 12 shows a perspective view of two implants implanted in a femur to restore sections of knee joints.

FIG. 12 shows two implants 10*a*, 100*b*, which are implanted in a knee joint of a femur 102. Implants 100*a,b* are made from of a titanium alloy that is commonly used for joint implants. The first frontal faces 104*a,b* of the implants form a part of joint surface 112 and are surface treated in such a way that they exactly match the surrounding joint surface 112 and represent the joint in its original functionality. The implants are secured in the interference fit in the holes drilled out of bone 102, so that they are restrained from axial movement even when the joint is stressed. Here it should be noted that the fact that frontal faces 104*a,b* of implants 100*a,b* are inclined at an angle not equal to 90 degrees relative to the cylinder axis of base 106*b* causes non-axial application of forces to the implant. In the figure, cylindrical base 106*b* of right implant 100*b* is clearly visible.

Figure 13:
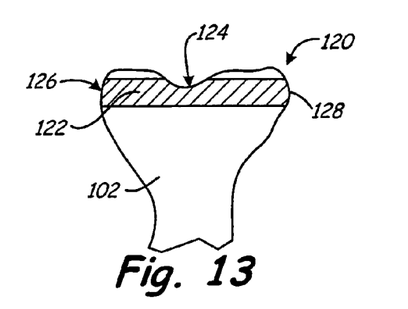
FIG. 13-16 shows additional embodiments of implants according to the invention.

FIG. 13 is a highly schematic representation of an implant 120 with a cylindrical base 122, in which joint replacement surface 124 is formed in the peripheral area of base 122, in other words by removing material in the peripheral area. Frontal faces 126, 128 close with the periphery of bone 102 in the joint area. The implant is preferably made from titanium alloy, but it may also be made from consist of another of the bone and/or joint replacement materials cited. In particular, joint replacement surface 124 may be arranged on a component that is to be inserted separately in base 122, which is a special joint replacement material.

Figure 14:
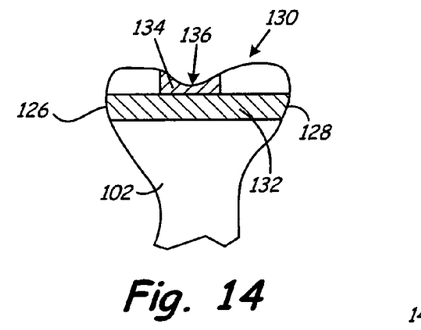

FIG. 14 shows an implant 130 with a cylindrical base 132 that has an adapter for a joint surface replacement part 134, on which joint replacement surface 136 is formed. Pins, screws, interference fit and others may serve as adapting means. The advantage of this embodiment resides in the fact that base 132 may be made from an optimized bone replacement material, while the joint surface replacement part 134 is optimized for the formation of the joint surface.

Figure 15:
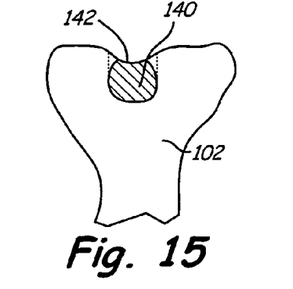

FIG. 15 shows a spherical implant 140, which is inserted in a cylindrical drill hole in the joint area of bone 102. Joint replacement area 142 has been created by removal from the sphere periphery.

Figure 16A:
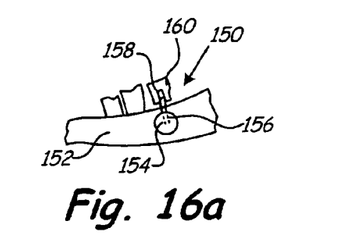
Figure 16B:
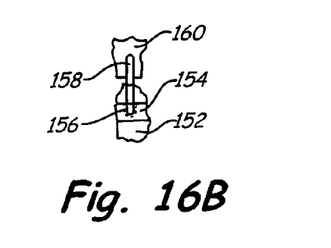

FIGS. 16*a* and 16*b* show an implant 150 in the jaw bone 152. The implant includes a circular cylindrical base 154, which is inserted with its longitudinal axis horizontal and crosswise to the jaw bone. Base 154 has an adapter 156, in the simplest case a drilled hole, in which a pin 158 is placed to receive a crown 160. Base 154 is preferably made of bone replacement material with good tissue tolerance, which is capable of growing especially well into the bone. The pin and the crown may be made from conventional dental implant materials.

The bases shown in the above figures preferably have a circular cylindrical shape. However, they may also have other shapes such as a ball, a cone or a cylinder with non-circular base, etc.

The examples shown in the figures are intended purely to explain the object of the invention and not designed to modify the scope of protection, which will be defined in the following claims.

Naturally, it is possible to provide individual features of the invention separately or in combinations thereof, e.g. the guide wires. If the method is carried out so that the drilling axis prescribed by the arrangement approximately intersects the center of the defective joint surface, deviations of a few mm, e.g. up to 5 mm are tolerable.

The invention claimed is:

1. An arrangement for partial restoration of joint surfaces including:
    an angle adjusting device in the form of elliptical plates of different diameters and intersection angles for covering a joint surface section to be restored for determining at least one of the angle and size of a replacement material to be implanted;
    an angle guiding device with
        a fixing extension for insertion between the joint surfaces;
    a second angle adjusting device linked with the fixing extension, which has at least one guide that is arranged at an angle relative to the fixing extension for setting at least one of a guide wire in an operation field and a bore guide for a tubular drill;
    a roller bearing mounted in the bore guide; and
  a drilling system including at least one of a drill and punch which can be guided through the bore guide, which bore guide is held either by one of the angle adjusting device and the guide wire at a set angle position relative to the joint surface section to be restored.

2. The arrangement as claimed in claim 1, characterised in that the drill of the drilling arrangement has a beveled tip.

3. The arrangement as claimed in claim 1, characterised in that the drill comprises a hollow cylindrical punch with a diamond runner back.

4. The arrangement as claims claimed in claim 1, characterised in that the drilling arrangement includes an oscillation drill with an oscillation angle of no more than 10 degrees.

5. The arrangement as claimed in claim 1, characterised in that the roller bearing has elements adapted to be fixed against the drill with a clamp.

6. The arrangement as claimed in claim 1, characterised in that the fixing extension is formed by a first elliptical plate and that the axis of one of the guide and bore guide at least substantially bisects the center of the first elliptical plate.

7. A tubular drilling device for surgical applications, especially prosthetics, including an oscillation drill machine with a small oscillation angle between about 1 to 25 degrees, and at least one drill with a beveled drill head wherein the bevel forms an elliptical surface of the drill head of the drill wherein an angle of the bevel is configured to be based upon the elliptical perimeter desired at an exit of a bore through a bone.

8. The tubular drilling device of claim 7, wherein the drill is a tubular drill.

9. The tubular drill as claimed in claim 8, characterised in that it is shaped as a hollow cylindrical drilling punch.

10. The tubular drill as claimed in claim 9, characterised in that the drilling punch has a runner back with at least one of a stone, diamond and carbide trim.

11. A set of angle adjusting plates for determining the size and angle setting of replacement materials for implanting in prosthetics, which angle determination plates have the form of elliptical plates with an elliptical perimeter, the shape of which plates is obtained by a diagonal cut through a circular cylinder, wherein the angle of intersection of different elliptical plates varies wherein each plate includes an upper substantially flat surface wherein the substantially flat surface is continuous and bound by the elliptical perimeter.

12. A set of angle determination plates as claimed in claim 11, characterised in that the width of the individual elliptical plates varies.

13. A tubular drilling device for surgical applications, especially prosthetics, comprising a tubular drill that is shaped as a hollow cylinder and has a bevelled tip, wherein the beveled tip forms an elliptical surface of a drill head of the drill around the perimeter of the drill, and further comprising a drilling machine configured to accept the tubular drill and provide power to the tubular drill, wherein the drilling machine is an oscillating drilling machine that oscillates at an angle between about 1 and 25 degrees.

* * * * *